ic Patent [19]

United States Patent [19]
Cleaver

[11] 3,944,668
[45] Mar. 16, 1976

[54] ANTIMICROBIAL COMPOSITIONS
[75] Inventor: David Frederick Cleaver, Hale Barns, England
[73] Assignee: Paterson Zochonis & Company, Limited, England
[22] Filed: Mar. 29, 1974
[21] Appl. No.: 456,199

[52] U.S. Cl. ............................................... 424/227
[51] Int. Cl.$^2$ ........................................ A61K 31/65
[58] Field of Search ............................ 424/227, 258

[56] References Cited
OTHER PUBLICATIONS
The Merck Index, 8 ed. Merck and Co., Inc., Rahway, N.J. 1968, pp. 247 and 1024.
Chemical Abstracts 65:5891 e (1966).

*Primary Examiner*—Jerome D. Goldberg
*Attorney, Agent, or Firm*—Wenderoth, Lind & Ponack

[57] ABSTRACT

The stability of tetracycline is improved by compounding it with 8 - hydroxyquinoline or a chlorinated and/or alkyl derivative thereof. In the compositions, which are particularly suitable for topical application, the tetracycline and the quinoline derivative are shown to behave synergistically against certain micro-organisms.

1 Claim, No Drawings

ANTIMICROBIAL COMPOSITIONS

This invention relates to tetracycline - based compositions for the treatment of microbial infections. The antibacterial activity of the tetracyclines is well known, but improved stability could be advantageous particularly in contact with air, particularly when in solution in water. Antimicrobial compositions comprising tetracycline in a variety of common pharmaceutical carriers, with improved shelf life particularly of opened and part-used product forms, e.g. multiple pack of impregnated wound dressings, would be of real use to the medical profession.

The present invention provides an antimicrobial composition comprising a tetracycline in a concentration to have an effective antibacterial action, 8-hydroxyquinoline or a chlorinated and/or alkyl derivative thereof in a concentration to stabilise the tetracycline, and a pharmaceutically acceptable diluent and/or carrier. Both the tetracycline and the quinoline derivative may be present as such or in the form of a salt.

By a tetracycline is meant a member of the class of antibiotics broadly known as tetracyclines such as tetracycline, oxytetracycline, chlortetracycline, dimethylchlortetracycline, doxycycline, methacycline and their salts such as hydrochlorides. The concentration of tetracycline to provide an effective antimicrobial action depends on the circumstances of use, but will often be in the range of 0.1 to 6%, preferably 1 to 3%, by weight on the weight of the composition.

As stabilising agents, there are particularly envisaged 8-hydroxyquinoline, 5-chloro-8-hydroxyquinoline, 5,7-dichloro-8-hydroxyquinoline, 5,7-dichloro-8-hydroxyquinaldine, their salts such as hydrochlorides and sodium salts, and mixtures thereof. The concentration required to stabise the tetracycline, by retarding or preventing decomposition thereof, again depends on the circumstances of use, but will often be in the range of 0.1 to 8%, particularly 1 to 3%, by weight on the weight of the composition. 8-Hydroxyquinoline itself is somewhat toxic compared to its chlorinated derivatives and is likely to be used in concentrations only towards the lower ends of these ranges. 5-chloro-7-iodo derivatives of 8-hydroxyquinoline may also be useful in cases where any liberated iodine does not accelerate decomposition of the tetracycline.

Preferably the ratio of the tetracycline to the 8-hydroxyquinoline or chlorinated and/or alkyl derivative thereof is between 3:1 and 1:3 by weight.

The compositions of this invention may be used for topical application to wounds, burns, ulcers, and topical infection, or for oral administration to combat internal infection.

In the treatment of surface wounds it is known that tetracyclines produce a good effect against a wide range of bacteria but that there is the possibility of contamination of the wound by mould spores or organisms resistant to tetracyclines. Such wounds as road accident abrasions are known to be very highly contaminated and have proved to be quite a problem as regards treatment with antibiotics. It has now been found that the incorporation of 5-chloro-8-hydroxyquinoline and other related 8-hydroxyquinolines into topical formulations with tetracycline, results in a product having, not only improved storage stability, but also synergistic activity against a wide spectrum of microorganisms,.

A preferred composition for such purposes comprises from 1 to 3% by weight of tetracycline, from 1 to 3% by weight of 5-chloro-8-hydroxyquinoline and a pharmaceutically acceptable diluent or carrier.

Compositions for internal application preferably comprises 5,7-dichloro-8-hydroxyquinoline as the stabilising agent.

8-Hydroxyquinoline and 8-hydroxyquinaldine derivatives are amphoteric and may therefore under some circumstances form salts with the tetracycline. It is believed, however, that the two active ingredients act separately, and that any salt formation that may take place does not adversely affect the antimicrobial properties of the composition.

The compositions may be prepared in the form of ointments, creams, lotions, passaries, powders and also spray pack formulations containing the active ingredients in solution or suspension.

The composition in the form of an ointment usually utilises a nonaqueous base material such as petrolatum. Such compositions in the form of ointments may be employed in the production of medicated dressings where a tulle prepared from say bleached cotton, cotton and rayon, or rayon is impregnated with the ointment.

For the treatment of oral infections and wounds such as ulcers where the composition may be in the form of an ointment, powder or lozenge the composition may also include suitable flavouring agents.

The compositions may also include anti-inflammatory drugs which are active when applied topically such as hydrocortisone. They may also include antioxidants such as sodium metabisulphite.

The invention is illustrated by the following non-limiting examples

EXAMPLE 1

A topical ointment was prepared having the following composition

|  | w/w |
|---|---|
| Tetracycline hydrochloride | 1% |
| 5-Chloro-8-hydroxyquinoline | 1% |
| Sodium metabisulphite | 0.2% |
| Yellow soft paraffin | to 100% |

EXAMPLE 2

A topical ointment was prepared having the following composition

|  | w/w |
|---|---|
| Tetracycline hydrochloride | 2% |
| 5-Chloro-8-hydroxyquinoline | 2% |
| Paraffin Wax | 5% |
| Antioxidant | q.s. |
| Yellow Soft Paraffin | to 100% |

EXAMPLE 3

A formulation having the following composition was prepared and used to impregnate a tulle:

|  | w/w |
|---|---|
| Tetracycline hydrochloride | 1% |
| 5-Chloro-8-hydroxyquinoline | 1% |
| Lanoline Anhydrous | 0.5% |

-continued

| | w/w |
|---|---|
| Paraffin Wax | 2% |
| Antioxidant | q.s. |
| Yellow Soft Paraffin | to 100% |

EXAMPLE 4

A topcial gel was prepared having the following composition

| | w/w |
|---|---|
| Tetracycline hydrochloride | 1% |
| 5-Chloro-8-hydroxyquinoline | 1% |
| Antioxidant | q.s. |
| Polyox WSR-205 (Union Carbide) | 2% |
| Propylene Glycol | 85% |
| Water | to 100% |

EXAMPLE 5

A sterile dusting powder was prepared having the following composition

| | w/w |
|---|---|
| Tetracycline hydrochloride | 2% |
| 5-Chloro-8-hydroxyquinoline | 1% |
| Antioxidant | q.s. |
| Sterile absorbable dusting powder | to 100% |

5,7-dichloro-8-hydroxyquinaldine can be used in place of 5-chloro-8-hydroxyquinoline.

EXAMPLE 6

A product for application in the form of an aerosol spray was prepared by filing into a 2 oz. aerosol container a concentrate containing

| | |
|---|---|
| Tetracycline Hydrochloride | 100 mg |
| 5-Chloro-8-hydroxyquinoline | 50 mg |
| Dipropylene Glycol | 20 ml | and then pressurizing the container by the addition as propellant of a mixture

| | |
|---|---|
| Propellent 11-S | 5 ml |
| Propellent 12 | 10 ml |

EXAMPLE 7

A powder in a form suitable for topical ulcer application was prepared having the following composition

| | w/w |
|---|---|
| Tetracycline | 1% |
| 5-Chloro-8-hydroxyquinoline | 1% |
| Natrosol micronised | 4% |
| Spray Dried Acacia | 3% |

-continued

| | w/w |
|---|---|
| Lactose | 90.5% |
| Menthol | 0.5% |
| Flavour/Antioxidant | q.s. |

EXAMPLE 8

Mouth lozenges were prepared each lozenge having the composition:

| | w/w |
|---|---|
| Oxytetracycline | 5 mg |
| 5-Chloro-8-hydroxyquinoline | 10 mg |
| Flavour/Antioxidant | q.s. |
| Sugar Base | to 1 gramme |

EXAMPLE 9

Pessaries were prepared, each pessary having the composition:

| | w/w |
|---|---|
| Tetracycline | 20 mg |
| 5-Chloro-8-hydroxyquinoline | 40 mg |
| Antioxidant | q.s. |
| Starch | 100 mg |
| Lactose | to 1 Gramme |

The antimicrobial activity and storage properties of the ointment of Example 1 (containing 1% tetracycline hydrochloride and 1% 5-chloro-8-hydroxyquinoline) was compared with a similar ointment containing 1% tetracycline hydrochloride.

Surprisingly it was found that the ointment (A) containing 1% tetracycline hydrochloride and 1% 5-chloro-8-hydroxyquinoline was rather more stable than the ointment (B) containing 1% tetracycline hydrochloride alone. Thus visual examination of samples stored in the absence of light for 3 months and 6 months at room temperature, 37°C and 45°C showed only slight colour change with the former but severe darkening with the latter.

| | Initial | Room temperature 3 month | 6 month | 37°C 3 month | 6 month | 45°C 3 month | 6 month |
|---|---|---|---|---|---|---|---|
| A | light-yellow | light-yellow | yellow | grey-yellow | yellow | grey-yellow | white-yellow |
| B | light-yellow | orange-yellow | orange-yellow | brown-yellow | red-yellow | brown-yellow | red-yellow |

Again on storage there was no evidence of evolved gases with the former ointment after storage at room temperature, 37°C or 45°C for 3 or 6 months whereas with the latter after storage at room temperature for 3 or 6 months there was a slight odour, and with samples stored for 3 or 6 month at 37°C or 45°C there was a strong odour.

The samples of ointment (A) and (B) stored at elevated temperatures for six months were examined by thin layer chromatography using cellulose plates. One gram samples of the ointments were washed with petroleum ether (b.p. 40°–60°C) thus removing the 5-chloro-8-hydroxyquinoline and the jelly base and leaving as a residue the tetracycline and any of its breakdown products. The residue was taken up in methanol (2 mls) chloroform (2mls) and water (10 drops) and fractionated on cellulose preparative thin layer chromatography plates eluting with ethyl acetate/isopropanol/water (70:40:20). The main breakdown product from the sample of ointment (B) stored at 37°C and 45°C was extracted from the plates and found to be equivalent to 5% and 8% respectively of the tetracycline. In these two samples of ointment (B) there was also a minor proportion of a second breakdown product. With the ointment (A) the evidence was that breakdown if any was negligible.

The microbiological properties of ointment (A) were compared with those ointments (B) and an ointment (C) (containing 1% 5-chloro-8-hydroxyquinoline) against a range of organisms isolated from clinical conditions.

Two tests were used to detect any bacteriostatic properties of the formulations.

Zone inhibition test

Pour plates were prepared, using 20 ml. nutrient agar containing 0.4 ml. culture. Plates were prepared for each culture tested. A well was cut in the centre of each plate which was then filled with the jelly under test. The plates were incubated at 37°C/48H. Clear zones of inhibition which had developed were measured.

Minimum Inhibitory Concentration Test 5g of jelly were added to 95 ml. nutrient broth and the mixture left overnight in an incubator at 37°C. This was done in order to improve the dispersion of the jelly in the nutrient broth and hence allow the antibiotic to deffuse into the liquid medium. At ambient temperature the jelly was completely immiscible in the broth.

The following day doubling dilutions of this 1 : 20 dilution were made to a final dilution of 1 : 10,240 i.e. a total of 10 dilutions were made in all.

Each dilution was incubated with 1 drop of 1 in 10 dilution of a 24 h. broth culture of organism under test and the tubes incubated at 37°C/72 h.

The minimum inhibitory concentration (MIC) of the jelly was the highest dilution which failed to allow growth of the organism.

From the MIC results and Zone inhibition results given in the table below, there is some evidence of synergism between the two agents against certain organisms, e.g. *Staphylococcus albus*, E. coli, some Proteus spp. and *Klebsiella aerogenes*.

TABLE

| Results: Culture | Antibiotic Sensitivity | | Inhibition test results on Jellies | | | | | |
|---|---|---|---|---|---|---|---|---|
| | | | Zone Inhibition Results Size of zone in mm | | | MIC results Lowest diln. prevening growth of Organism: | | |
| | Tetracycline | CHQ | A | B | C | A 1: | B 1: | C 1: |
| Coliform 518 | S | S | 8* | 3 | 5 | <20 | 80 | <20 |
| Coliform 608 | S | S | 5 | 5 | 5 | <20 | 20 | <20 |
| Coliform 578 | S | S | 6 | 0 | 6 | 160 | <20 | 320 |
| E. coli 566 | S | S | 7* | 3 | 5 | <20 | <20 | <20 |
| E. coli 559 | S | S | 16* | 4 | 9 | 80 | <20 | 80 |
| E. coli 604 | S | S | 8 | 6 | 7 | 80 | <20 | 160 |
| E. coli 026 | R | S | 4 | 0 | 3 | 20* | <20 | <20 |
| E. coli 9395 | S | S | 10* | 3 | 3 | 80* | 20 | <20 |
| Proteus 371 | SS | S | 6 | 0 | 6 | 160* | <20 | <20 |
| Proteus 20522 | SS | S | 5 | 0 | 5 | <20 | <20 | <20 |
| Proteus 20029 | SS | S | 6* | 0 | 4 | <20 | <20 | 80 |
| Proteus 20523 | SS | S | 6 | 0 | 6 | <20 | <20 | 20 |
| Proteus 20531 | SS | S | 2 | 0 | 2 | <20 | <20 | <20 |
| Pr. mirabilis 5887 | SS | S | 2 | 0 | 2 | <20 | <20 | <20 |
| Pr. mirabilis 25942 | SS | S | 7 | 0 | 7 | <20 | <20 | <20 |
| Pr. rettgeri 7475 | S | S | 7* | 5 | 3 | 80* | <20 | <20 |
| Pr. vulgaris 4635 | S | S | 9* | 2 | 4 | 40* | <20 | <20 |
| Pr. miribilis 25702 | S | S | 0 | 0 | 0 | <20 | <20 | <20 |
| Ps. multivorans BS | S | S | 0 | 0 | 0 | <20 | <20 | <20 |
| Ps. multivorans MB | S | S | 11 | 7 | 16 | 40* | <20 | <20 |
| Ps. aeruginosa 5267 | S | R | 0 | 0 | 0 | <20 | <20 | <20 |
| Ps. aeruginosa 1999 | S | R | 0 | 0 | 0 | <20 | <20 | <20 |
| Kleb, aerogenes 8172 | S | S | 14 | 7 | 13 | 640* | 160 | 20 |
| Kleb. aerogenes 22352 | S | S | 8 | 5 | 8 | 40* | <20 | <20 |
| Serratia marcescens | S | S | 2* | 0 | 0 | <20 | <20 | <20 |
| Strep. faecalis 20190 | R | S | 5* | 0 | 3 | 20 | <20 | 80 |
| Strep. faecalia 559 | R | S | 0 | 0 | 2 | 20 | <20 | <20 |
| Staph. albus 474 | R | S | 6 | 0 | 5 | <20 | <20 | <20 |
| Staph. albus 476 | R | S | 6 | 0 | 6 | 80* | <20 | 20 |
| Staph. albus 473 | R | S | 6 | 0 | 5 | 80* | <20 | 20 |
| Staph. albus 479 | R | S | 6 | 0 | 4 | 40 | <20 | 40 |
| Staph. aureus 20477 | R | S | 4* | 0 | 2 | 40 | <20 | 20 |
| Staph. aureus 590 | R | S | 5 | 0 | 4 | 160* | <20 | 40 |
| Staph. pyogenes | R | S | 7 | 0 | 6 | 40 | <20 | <20 |
| Staph. aureus 7447 | S | S | 9* | 5 | 7 | 1280 | <20 | 1280 |
| Candida albicans | R | S | 19 | 0 | 20 | 40 | <20 | 40 |

R = resistant.
S = sensitive.
SS = slightly sensitive
*suggests possible synergistic effect between tetracycline hydrochloride and 5 monochlor 8- hydroxyquinoline.

EXAMPLE 10

A 1% by weight solution of tetracycline hydrochloride in water was divided into three parts. To the first part there was added 1% by weight of 5-chloro-8-hydroxyquinoline. To the second part there was added 1%, by weight of 5,7-dichloro-8-hydroxyquinoline. No addition was made to the third part. The three aqueous compositions were then stored at 37°C in air. Decomposition of tetracyline in the third part was quite rapid, and a brown colour developed within a week. The other two parts showed good stability after one weeks storage. It appears that the decomposition of tetracyline in aqueous solution is materially slowed down in the presence of chlorinated derivatives of 8-hydroxyquinoline.

In the Examples:-

Polyox W S R - 205 is believed to be a polyoxyethylene glycol.

Natrosol is a hydroxyethylcellulose.

What we claim is:

1. A stable antimicrobial composition for topical or oral application comprising from 1 to 3% of tetracycline, from 1 to 3% of 5-chloro-8-hydroxyquinoline or 5,7-chloro-8-hydroxyquinoline and a pharmaceutically acceptable diluent or carrier.

* * * * *